(12) United States Patent
Achatz et al.

(10) Patent No.: US 11,810,663 B2
(45) Date of Patent: *Nov. 7, 2023

(54) SIMULATING A TARGET COVERAGE FOR DEEP BRAIN STIMULATION

(71) Applicant: Brainlab AG, Munich (DE)

(72) Inventors: Stefan Achatz, Freising (DE); Bálint Varkuti, Munich (DE)

(73) Assignee: BRAINLAB AG, Munich (DE)

(*) Notice: Subject to any disclaimer, the term of this patent is extended or adjusted under 35 U.S.C. 154(b) by 0 days.

This patent is subject to a terminal disclaimer.

(21) Appl. No.: 17/957,462

(22) Filed: Sep. 30, 2022

(65) Prior Publication Data
US 2023/0099535 A1   Mar. 30, 2023

Related U.S. Application Data

(63) Continuation of application No. 16/828,484, filed on Mar. 24, 2020, now Pat. No. 11,495,345, which is a
(Continued)

(30) Foreign Application Priority Data

Dec. 16, 2015   (WO) .................. PCT/EP2015/079917

(51) Int. Cl.
G09G 5/00       (2006.01)
G16H 30/40      (2018.01)
(Continued)

(52) U.S. Cl.
CPC ........... G16H 30/40 (2018.01); A61N 1/0534 (2013.01); A61N 1/36185 (2013.01);
(Continued)

(58) Field of Classification Search
CPC ........ G16H 30/40; G16H 20/30; G16H 30/20; G16H 50/50; A61N 1/0534;
(Continued)

(56) References Cited

U.S. PATENT DOCUMENTS 9,974,959 B2 *  5/2018  Moffitt ............... A61N 1/37235
10,639,471 B2   5/2020  Achatz et al.
(Continued)

FOREIGN PATENT DOCUMENTS

WO   2015196164 A2   12/2015

OTHER PUBLICATIONS

Extended European Search Report for European Patent Application No. 1700250.5 dated Jun. 20, 2017; 7 pages.

*Primary Examiner* — Maroun P Kanaan
(74) *Attorney, Agent, or Firm* — Gray Ice Higdon

(57) ABSTRACT

A system is disclosed for determining a coverage of a target anatomical structure by an electric stimulation field. The system includes a computer to acquire patient image data and the atlas data, determine, based on the patient image data and the atlas data, target structure position data describing a position of the target anatomical structure in the medical image of the anatomical body part of the patient. The system also acquires electrode position data and stimulation field data describing an electric stimulation field around the position of the electrode. The system also includes an electrode configuring device for adjusting an emission configuration of the electrode.

20 Claims, 2 Drawing Sheets

Related U.S. Application Data continuation of application No. 15/431,575, filed on Feb. 13, 2017, now Pat. No. 10,639,471.

(51) Int. Cl.
*G06F 16/50* (2019.01)
*A61N 1/372* (2006.01)
*G16H 50/50* (2018.01)
*G16H 30/20* (2018.01)
*G16H 20/30* (2018.01)
*A61N 1/05* (2006.01)
*A61N 1/36* (2006.01)

(52) U.S. Cl.
CPC ..... *A61N 1/37235* (2013.01); *A61N 1/37241* (2013.01); *A61N 1/37247* (2013.01); *G06F 16/50* (2019.01); *G16H 20/30* (2018.01); *G16H 30/20* (2018.01); *G16H 50/50* (2018.01)

(58) Field of Classification Search
CPC ............ A61N 1/36185; A61N 1/37235; A61N 1/37241; A61N 1/37247; G06F 16/50
See application file for complete search history.

(56) References Cited

U.S. PATENT DOCUMENTS

| | | |
|---|---|---|
| 2012/0302912 A1 | 11/2012 | Moffitt et al. |
| 2014/0163660 A1 | 6/2014 | Fang et al. |
| 2018/0296277 A1* | 10/2018 | Schwartz ............... G16H 10/60 |
| 2020/0222690 A1 | 7/2020 | Achatz et al. |

* cited by examiner

1

SIMULATING A TARGET COVERAGE FOR DEEP BRAIN STIMULATION

The present invention is directed to a computer-implemented method for determining a coverage of a target anatomical structure by an electric stimulation field, a corresponding computer program, a non-transitory program storage medium storing such a program and a system comprising a computer for executing the program, as well as a medical procedure planning system comprising a database and such a computer.

TECHNICAL BACKGROUND

Electric deep-brain stimulation (DBS) is generally used for therapy of neurological diseases such as Parkinson's disease. DBS involves placing an electrode inside the brain and applying, via the electrode, an electric stimulation field to functional areas of the brain so as to counteract brain malfunctions which lead to the symptoms to be treated. The extent and strength of the stimulation field should be configured in space and time so as to influence only relevant parts of the brain, i.e. a target structure which shall be the target of the therapy. A problem associated with finding a suitable configuration of the stimulation is field is that so far such a configuration could only be found out by trial-and-error on a living patient. For example, the electrode is placed inside the brain, and the stimulation field is activated. A physician then evaluates the patient's physical response, for example by monitoring a decrease in disease symptoms or other neurological reactions, such as movements of specific body parts (e.g. eyes, hands, or legs) in response to activating the stimulation field. Only on the basis of results received from such a trial-and-error procedure can a brain stimulation device (which the patient carries with him for example as an implant) be programmed to emit the desired electric stimulation field. Such a procedure is cumbersome and specifically associated with a certain risk for the patient due to the necessity of introducing the electrode, which also leads to considerable costs for running the trials.

An object of the invention therefore is to provide a more efficient method of determining a desired configuration of an electric stimulation field.

Aspects of the present invention, examples and exemplary steps and their embodiments are disclosed in the following. Different advantageous features can be combined in accordance with the invention wherever technically expedient and feasible.

EXEMPLARY SHORT DESCRIPTION OF THE PRESENT INVENTION

In the following, a short description of the specific features of the present invention is given which shall not be understood to limit the invention only to the features or a combination of the features described in this section.

The disclosed method encompasses using a match between a medical image of a patient and an atlas of a corresponding anatomical body part for determining a target of the electric stimulation therapy, defining the position of a for example directional electrode in relative to the target and simulating the electric stimulation field around the position of the electrode in order to determine the coverage of the target by the electric stimulation field. The control parameters for controlling the electric stimulation field (which include the position of the electrode relative to the target) may be varied until a desired coverage of the target by the electric stimulation field is achieved.

GENERAL DESCRIPTION OF THE PRESENT INVENTION

In this section, a description of the general features of the present invention is given for example by referring to possible embodiments of the invention.

In general, the invention reaches the aforementioned object by providing, in a first aspect, a computer-implemented method for determining a coverage of a target anatomical structure by an electric stimulation field. The method comprises executing, on at least one processor of at least one computer, steps of the following exemplary steps which are executed by the at least one processor.

In a (for example first) exemplary step, patient image data is acquired which describes (for example, represents or defines) a medical image of the anatomical body part of a patient, wherein the anatomical body part includes the target anatomical structure. The anatomical body part may be any part of the patient's body and in one example includes or is the brain. The target anatomical structure then may be a specific functional area of the brain. The patient image data has for example been generated before the disclosed method is executed; alternatively, generating the patient image data may be done as part of the disclosed method. The patient image data is medical image data which has been generated by applying a medical imaging method (a medical imaging modality) such as computed x-ray tomography (CT) or magnetic resonance tomography (MR/MRT) to the anatomical body part and generating a digital image representing the medical image of the anatomical body part. The patient image data is for example generated before an electrode for applying an electric stimulation field is inserted into the anatomical body part.

In a further (for example second) exemplary step, atlas data is acquired which describes (for example, represents or defines) a model of the anatomical body part and information about (i.e. defining) the position of a model target structure in the model of the anatomical body part, the model target structure corresponding (at least in anatomical/physiological function) to the target anatomical structure. The model of the anatomical body part for example is an image-based model, i.e. it may have been generated on the basis of medical image data acquired for the corresponding anatomical body part of a multitude of patients. Such medical image data may have been generated by applying the same medical imaging modality as for generation of the patient image data or by applying another medical imaging modality. In the latter case, the atlas data may represent a multi-modal model (multi-modal atlas) which contains a mapping between greyscale representations of different tissue types (tissue classes) defined for different medical imaging modalities (for example, the same kind of body tissue may have an image appearance in a CT slice image which differs from its appearance in an MR slice image). Thus, the model of the anatomical body part is for example suitable for comparison with medical image data taken with two different medical imaging modalities, wherein the atlas data describes for example a multi-modal atlas of the anatomical body part. The atlas data may also comprise information about the reaction of certain (functional) areas of the brain to electric stimulation.

In a further (for example third) exemplary step, target structure position data is determined which describes (for example, represents or defines) a position of the target anatomical structure in the medical image of the anatomical body part of the patient. The target structure position data is determined based on the patient image data and the atlas data. This can be embodied by an example of the disclosed method in which the step of determining the target structure position data includes determining, based on the patient image data and the atlas data, body part transformation data describing a positional transformation between the medical image of the anatomical body part and the model of the anatomical body part. This may include determining a transformation between the reference systems (coordinate systems) for defining positions in the atlas data (specifically, in the model of the anatomical body part) and the patient image data (specifically, in the medical image). The transformation may be a mapping such as a linear transformation between the reference systems and hence the individual positional coordinates. For example, the atlas data is matched to the patient image data, e.g. by applying an elastic or rigid image fusion algorithm to the atlas data and the patient image data (such as fusing the atlas data to the patient image data). Such a matching leads to establishing the mapping between the model of the anatomical body part and a corresponding anatomical structure (such as the anatomical body part) represented in the medical image defined by the patient image data. Using the mapping (or the inverse mapping, respectively), the position of an anatomical structure in the model of the anatomical body part corresponding to the target anatomical structure in the medical image is acquired. For example, a user inputs information defining the position of the respective anatomical structure in the model be delineating a corresponding part of an image representation of the model (e.g. by using a pointing tool such as a mouse or pa pointer on a touch screen). Alternatively, the position of the anatomical structure in the model may be predetermined in a treatment plan and a corresponding dataset may be acquired by the disclosed method. The position of target anatomical structure in the medical image is then determined by mapping the coordinates about the anatomical structure selected in the model into the reference system in which positions in the medical image are defined. The result of that mapping is assumed to be the position of the target anatomical structure in the medical image.

In a further (for example fourth) exemplary step, electrode position data is acquired which describes (for example, represents or defines) a relative position between a position of an electrode (an electric stimulation electrode) and a position of the anatomical body part of the patient as it is described by the patient image data (i.e. in the medical image). Specifically, information about the position of the electrode in the anatomical body part is acquired as a predetermined dataset or by user input (for example, by inputting numeric values for the positional coordinates of the electrode or by drawing them—e.g. by using a drawing/pointing tool or a touch screen—into the medical image). Thereby, information about the relative position between the position of the electrode and the position of the target anatomical structure in the medical image can be determined within the disclosed method. The electrode in one example is represented as a directional electrode having a plurality of electrically emitting contacts. The representation electrode in one example comprises a representation of a marker (which is assumed to be visible in a medical image of a real electrode, such as a metal plate affixed to the electrode) to determine the orientation of the electrode specifically in the medical image (at least relative to target anatomical structure).

In a further (for example fifth) exemplary step, stimulation field data is acquired which describes (for example, represents or defines) an electric stimulation field around the position of the electrode. The electric stimulation field for example is or may be made suitable for electric stimulation of the target anatomical structure. The electric stimulation field is defined by for example at least one of its position and orientation relative to the position of the electrode and/or the target anatomical structure. Furthermore, the electric stimulation field may be defined by its spatial electric or magnetic energy distribution (its electric or magnetic field strength) in space and time (for example, the field strength may be constant in both space and time, or constant in time and variable in space, or constant in both space and time). If the electrode has a plurality of contacts for emitting the electric stimulation field, the electric stimulation field may be automatically adjusted by adjusting a distribution of electric energy onto the contacts (for example, by individually adjusting the electric current to be applied to each contact). This can be done for example by acquiring a predetermined dataset comprising corresponding information or user input of corresponding information (for example, by manually inputting numeric values for each of the contacts which define the physical values such as at least one of the electric current, pulse width, rate to be applied to and the position of the electric stimulation field to be emitted by each of the contacts). Information which has been acquired may be changed thereafter for example by manual user input.

In a further (for example sixth) exemplary step, target coverage data is determined which describes (for example, represents or defines) a coverage of the target anatomical structure by the electric stimulation field. The target coverage data is determined based on the patient image data and the atlas data and the electrode position data and the stimulation field data. The target coverage data may be determined based further on the above-described body part transformation data. For example, the stimulation field data is analyzed whether the spatial extent of the simulated electric stimulation field includes the position of the target anatomical structure. The term of coverage denotes for example a spatial overlap between the electric stimulation field and the target anatomical structure. That overlap may be complete (i.e. the target anatomical structure may completely lie within the electric stimulation field) or partial (i.e. only part of and less than the entire target anatomical structure may lie within the electric stimulation field) or none at all (i.e. the electric stimulation field and the target anatomical structure may be spatially disjunct).

In a further embodiment, the disclosed method comprises:
  acquiring electrode image data describing (for example, representing or defining) a second medical image of the electrode (i.e. of a real electrode which has been implanted and imaged using a medical imaging modality such as CT or MR, the electrode having for example a marker visible in the second medical, such as a metal plate affixed to the electrode, for defining the orientation of the electrode) in the anatomical body part of the patient and specifically a relative position between the position of the electrode and the position of the anatomical body part in the second medical image;
  determining, based on the electrode image data and the atlas data, electrode transformation data describing (for example, representing or defining) a positional transformation between the position of the anatomical body part as it is described by the second medical image and the position of the model of the anatomical body part (this may be done by establishing a mapping between the positional information contained in the second medical image and the positional information contained the model, for example by applying an elastic or rigid image fusion algorithm to the electrode image data and the atlas data so as to e.g. fuse the atlas data to the electrode image data—one exemplary procedure for doing this is described above in connection with determining the target structure position data);

wherein the electrode position data is determined, by the processor, based on the electrode image data and the electrode transformation data and the body part transformation data (for example, by sequentially applying the transformation described by the body part transformation data and the transformation described by the electrode transformation data to the position of the electrode described by the electrode image data). The electrode position data may then be used for simulating the electric stimulation field emitted by an already implanted electrode.

In a further embodiment, the disclosed method comprises:

determining, based on the patient image data and the target structure position data and the electrode position data, electrode target data describing (for example, representing or defining) a relative position between the position of the target anatomical structure and the position of the (real) electrode (for example, by establishing a transformation between the position of the target anatomical structure and the position of the (real) electrode, which may be done by applying an elastic or rigid image fusion algorithm to the electrode data and the patient image data, the position of the target anatomical structure in the medical image being known from the target structure position data);

wherein the target coverage data is determined further based on the electrode target data (for example, by using the relative position described by the electrode target data for determining whether the position of the target anatomical structure is within the spatial extent of the electric stimulation field simulated using the position of the imaged [implanted] electrode).

In a further embodiment, the disclosed method comprises:

acquiring desired coverage data describing (for example, representing or defining) a desired coverage of the target anatomical structure by the electric stimulation field (for example, a desired extent to which the target anatomical structure should be covered by an electric stimulation field specifically for the envisaged therapeutic procedure);

determining coverage difference data describing a difference between the coverage described by the target coverage data and coverage described by the desired coverage data (for example, by determining a difference in at least one of position and volume of the coverage described by the target coverage data and the coverage described by the desired coverage data);

varying (e.g. automatically or by user input of changed physical values defining the electric stimulation field which may also include the position of the electrode relative to the target anatomical structure) the stimulation field data in order to optimize, for example minimize, the difference (so as to achieve an optimum coverage).

In a second aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect.

In a third aspect, the invention is directed to a non-transitory computer-readable program storage medium on which the program according to the second aspect is stored.

In a fourth aspect, the invention is directed to at least one computer (for example, a computer), comprising at least one processor (for example, a processor) and at least one memory (for example, a memory), wherein the program according to the second aspect is running on the processor or is loaded into the memory, or wherein the at least one computer comprises the program storage medium according to the third aspect.

In a fifth aspect, the invention is directed to a system for determining a coverage of a target anatomical structure by an electric stimulation field, the system comprising the at least one computer in accordance with the fourth aspect; an electrode configuring device for adjusting an emission configuration of the electrode; and at least one electronic data storage device storing at least one database comprising the patient image data, the atlas data and the electrode position data, wherein the at least one computer is operably coupled to the at least one database for acquiring, from the at least one database, the patient image data, the atlas data and the electrode position data; and wherein the at least one computer is operatively coupled to the electrode configuring device for transmission of the stimulation field data to the electrode configuring device in order to configure the electrode to emit the electric stimulation field described by the stimulation field data. The electrode configuring device may be specifically adapted for programming a brain pacemaker so that it controls an electric stimulation electrode to emit the electric stimulation field defined by the stimulation field data.

It is within the scope of the present invention to combine one or more features of one or more embodiments or aspects of the invention in order to form a new embodiment wherever this is technically expedient and/or feasible. Specifically, a feature of one embodiment which has the same or a similar function to another feature of another embodiment can be exchanged with said other feature, and a feature of one embodiment which adds an additional function to another embodiment can for example be added to said other embodiment.

Definitions

In this section, definitions for specific terminology used in this disclosure are offered which also form part of the present disclosure.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electric, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the computer implemented method or program, for example from another program, a previous method step or a data storage medium, for example for further processing by the computer implemented method or program. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Atlas data describes (for example defines, more particularly represents and/or is) a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

The present invention relates to the field of controlling a treatment beam. The treatment beam treats body parts which are to be treated and which are referred to in the following as "treatment body parts". These body parts are for example parts of a patient's body, i.e. anatomical body parts.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

In this application, the term "image morphing" is also used as an alternative to the term "elastic image fusion", but with the same meaning.

Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are for example vectors of a deformation field. These vectors are determined by the optimisation algorithm in such a way as to result in an optimum degree of similarity. Thus, the optimum degree of similarity represents a condition, for example a constraint, for the optimisation algorithm. The bases of the vectors lie for example at voxel positions of one of the first and second images which is to be transformed, and the tips of the vectors lie at the corresponding voxel positions in the transformed image. A plurality of these vectors is preferably provided, for instance more than twenty or a hundred or a thousand or ten thousand, etc. Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimising problem is for example solved iteratively, for example by means of an optimisation algorithm which is for example a first-order optimisation algorithm, such as a gradient descent algorithm. Other examples of optimisation algorithms include optimisation algorithms which do not use derivations, such as the downhill simplex algorithm, or algorithms which use higher-order derivatives such as Newton-like algorithms. The optimisation algorithm preferably performs a local optimisation. If there is a plurality of local optima, global algorithms such as simulated annealing or generic algorithms can be used. In the case of linear optimisation problems, the simplex method can for instance be used.

In the steps of the optimisation algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighbouring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can for example be determined on the basis of a determined correlation between the first and second datasets.

DESCRIPTION OF THE FIGURES

In the following, the invention is described with reference to the appended figures which represent a specific embodiment of the invention. The scope of the invention is however not limited to the specific features disclosed in the context of the figures, wherein

FIG. 1 shows the flow of the disclosed method. In step S1, the patient image data is acquired which involves loading a set of medical image data describing the anatomical body part. In step S2, the atlas data is acquired by loading a corresponding dataset. In subsequent step S3, the target structure position data is determined by for example drawing or segmenting a selected area in an image representation of the model of the anatomical body part in order to define an area in the model which corresponds to the target anatomical structure (which shall be covered by the electric stimulation field), and then performing image fusion between the medical image described by the patient image data and the model of the anatomical body part described by the atlas data. In step S4, the position of the electrode relative to the position of the target anatomical structure is defined by acquiring the electrode position data. In step S5, the stimulation field data is determined on the basis of previously acquired steering parameters for controlling the electric stimulation field emitted from the positions of contacts on the electrode. The steering parameters represent physical variables governing the geometry and energy distribution of the electric stimulation field. On the basis of the above, the target coverage data is determined in step S6. The steering parameters may be varied in order to achieve a desired (optimal) coverage of the target anatomical structure by the electric stimulation field.

Figure 1:
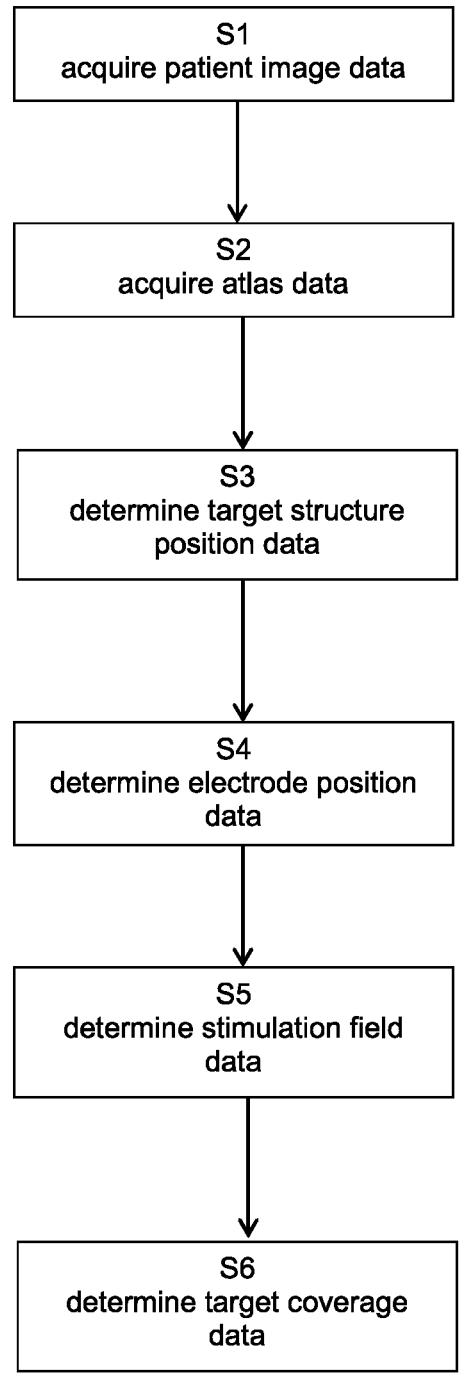
FIG. 1 is a flow diagram showing the steps of the disclosed method.
Figure 2:
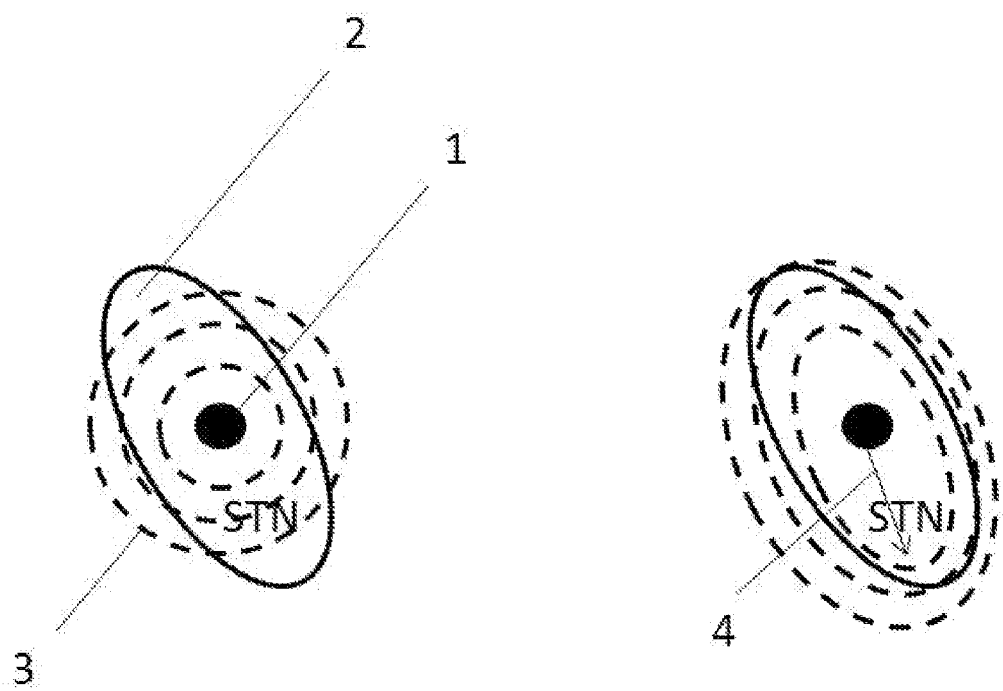
FIG. 2 is an illustration of how the coverage of a functional area of the brain by the electric stimulation field may be varied.

The left half of FIG. 2 illustrates a medical image showing the position of an electrode 1 placed in an anatomical body part 2 represented by the sub-thalamic nucleus (STN). The electric stimulation field 3 is represented by isoelectric lines around the position of the electrode 1. The right half of FIG. 2 shows what happens if the steering parameters for controlling the electric stimulation field 3 are varied, for example to extend the coverage in the direction defined by arrow 4 towards a target anatomical structure situated in the depicted lower-right part of the STN. This may be done by appropriately varying steering parameters for individual contacts on the directional electrode 4 which shall emit the electric stimulation field. This is done specifically in knowledge of the orientation of the directional electrode 1 so that the orientation (for example, rotational orientation) of each contact relative to the target anatomical structure is known. The process of achieving a desired coverage includes fanning or focusing, respectively, the electric stimulation field as well as rotation of the electric stimulation field around the z-axis (longitudinal axis) of the electrode 1.

The disclosed method provides the advantage of being able to simulate the effects of a specific configuration of an electric stimulation field without having to implant an electrode for example into the brain. This advantage is due to at least using atlas data as an input to the method which allows to determine the position of the target anatomical structure.

The invention claimed is:

1. A computer implemented method to adjust emissions of a medical electrode, comprising:
   acquiring patient image data and atlas data;
   determining, based on the patient image data and the atlas data, target structure position data describing a position of a target anatomical structure in a medical image of an anatomical body part of a patient;
   acquiring electrode position data describing a position of the medical electrode;
   acquiring electric field data describing an electric field around the position of the medical electrode;
   determining, based on the patient image data and the atlas data and the electrode position data and the electric field data, target coverage data describing a coverage of the target anatomical structure by the electric field; and
   determining, based on the patient image data and the atlas data, body part transformation data describing a positional transformation between the medical image of the anatomical body part and a model of the anatomical body part, wherein the target coverage data is determined further based on the body part transformation data,
      wherein the target coverage data is determined for use in covering the target anatomical structure by the electric field of the medical electrode, and adjusting an emission configuration of the medical electrode with an electrode configuring device.

2. The method of claim 1, wherein the position of the medical electrode is a relative position of the medical electrode with respect to a position of the anatomical body part of the patient as described by the patient image data.

3. The method of claim 1, wherein the model of the anatomical body part is an image-based model generated from a statistical analysis of images taken for a plurality of patients.

4. The method of claim 1, wherein the body part transformation data is determined by applying an image fusion algorithm to the patient image data and the atlas data.

5. The method of claim 1, wherein the medical electrode is a directional electrode having a plurality of electrically emitting contacts, and wherein the electric field is adjusted by adjusting a distribution of electric energy onto the plurality of electrically emitting contacts.

6. The method of claim 1, further comprising:
   acquiring electrode image data describing a second medical image of the electrode in the anatomical body part of the patient and specifically a relative position between the position of the medical electrode and the position of the anatomical body part in the second medical image; and
   determining, based on the electrode image data and the atlas data, electrode transformation data describing a positional transformation between the position of the anatomical body part as described by the second medical image and the position of the model of the anatomical body part,
   wherein the electrode position data is determined based on the electrode image data and the electrode transformation data and the body part transformation data.

7. The method of claim 6, wherein the electrode transformation data is determined by applying an image fusion algorithm to the electrode image data and the atlas data.

8. The method of claim 1, wherein the model of the anatomical body part is suitable for comparison with medical image data taken with two different medical imaging modalities, wherein the atlas data describes a multi-modal atlas of the anatomical body part.

9. The method of claim 1, further comprising:
   determining, based on the patient image data and the target structure position data and the electrode position data, electrode target data describing a relative position between the position of the target anatomical structure and the position of the medical electrode,
   wherein the target coverage data is determined further based on the electrode target data.

10. The method of claim 1, further comprising:
    acquiring desired coverage data describing a desired coverage of the target anatomical structure by the electric field; and
    determining coverage difference data describing a difference between the coverage described by the target coverage data and the coverage described by the desired coverage data;
    varying the electric field data to optimize the difference.

11. The method of claim 1, wherein the electric field data is acquired based on user input.

12. The method of claim 11, wherein the user input is manual input of physical values defining the electric field.

13. The method of claim 1, wherein the electric field data is acquired based upon predetermined datasets.

14. A system comprising one or more processors and memory storing instructions that, when executed, cause the one or more processor to perform operations comprising:
    acquiring patient image data and atlas data;
    determining, based on the patient image data and the atlas data, target structure position data describing a position of a target anatomical structure in a medical image of an anatomical body part of a patient;
    acquiring electrode position data describing a position of a medical electrode;
    acquiring electric field data describing an electric field around the position of the medical electrode;
    determining, based on the patient image data and the atlas data and the electrode position data and the electric field data, target coverage data describing a coverage of the target anatomical structure by the electric field; and determining, based on the patient image data and the atlas data, body part transformation data describing a positional transformation between the medical image of the anatomical body part and a model of the anatomical body part, wherein the target coverage data is determined further based on the body part transformation data, wherein the target coverage data is determined for use in covering the target anatomical structure by the electric field of the medical electrode, and adjusting an emission configuration of the medical electrode with an electrode configuring device.

15. The system of claim 14, wherein the position of the medical electrode is a relative position of the medical electrode with respect to a position of the anatomical body part of the patient as described by the patient image data.

16. The system of claim 14, wherein the model of the anatomical body part is an image-based model generated from a statistical analysis of images taken for a plurality of patients.

17. The system of claim 14, wherein the body part transformation data is determined by applying an image fusion algorithm to the patient image data and the atlas data.

18. The system of claim 14, wherein the medical electrode is a directional electrode having a plurality of electrically emitting contacts, and wherein the electric field is adjusted by adjusting a distribution of electric energy onto the plurality of electrically emitting contacts.

19. The system of claim 14, wherein the one or more processors are further configured to perform operations of:

acquiring electrode image data describing a second medical image of the medical electrode in the anatomical body part of the patient and specifically a relative position between the position of the medical electrode and the position of the anatomical body part in the second medical image; and determining, based on the electrode image data and the atlas data, electrode transformation data describing a positional transformation between the position of the anatomical body part as described by the second medical image and the position of the model of the anatomical body part, wherein the electrode position data is determined based on the electrode image data and the electrode transformation data and the body part transformation data.

20. The system of claim 14, wherein the electrode transformation data is determined by applying an image fusion algorithm to the electrode image data and the atlas data.

\* \* \* \* \*